United States Patent [19]

Manzella

[11] 4,359,057
[45] Nov. 16, 1982

[54] APPARATUS FOR MEASURING OXYGEN CONSUMPTION AND THE EXCHANGE OF OTHER BREATHING GASES

[76] Inventor: Giovanni Manzella, Via del Pratello, 13 - Bologna, Italy

[21] Appl. No.: 192,565

[22] Filed: Sep. 30, 1980

[51] Int. Cl.³ .............................................. A61B 5/08
[52] U.S. Cl. ................................... 128/718; 128/719; 128/728
[58] Field of Search ............... 128/716, 718, 719, 725, 128/727, 728

[56] References Cited

U.S. PATENT DOCUMENTS

| | | | |
|---|---|---|---|
| 2,592,694 | 4/1952 | Heidbrink | 128/718 |
| 2,630,798 | 3/1953 | White et al. | 128/718 |
| 3,401,683 | 9/1968 | Webb et al. | 128/718 |
| 3,523,529 | 8/1970 | Kissen | 128/718 |
| 3,698,384 | 10/1972 | Jones | 128/718 |
| 3,799,149 | 3/1974 | Rummel et al. | 128/718 |
| 3,875,626 | 4/1975 | Tysk et al. | 129/728 |
| 3,895,630 | 7/1975 | Backman | 128/719 X |
| 4,211,239 | 7/1980 | Raemer et al. | 128/718 X |

OTHER PUBLICATIONS

Michels et al., Annual Conf. on Eng. in Med. & Biology, 30th Acemb., L.A., Calif., Nov. 5-9, 1977, p. 19.

Primary Examiner—Kyle L. Howell
Assistant Examiner—John C. Hanley
Attorney, Agent, or Firm—Guido Modiano; Albert Josif

[57] ABSTRACT

An apparatus for measuring the oxygen consumption and the exchange of other breathing gases comprises an inflatable bag for collecting therein the gas exhaled by a patient, a main pneumatic circuit for coupling the bag to the patient, an auxiliary pneumatic circuit for the passage of a reference gas therethrough, a fuel-cell oxygen concentration sensor for analyzing the percentage of the gas being measured and a counter for counting the filling and emptying times of the bag.

4 Claims, 5 Drawing Figures

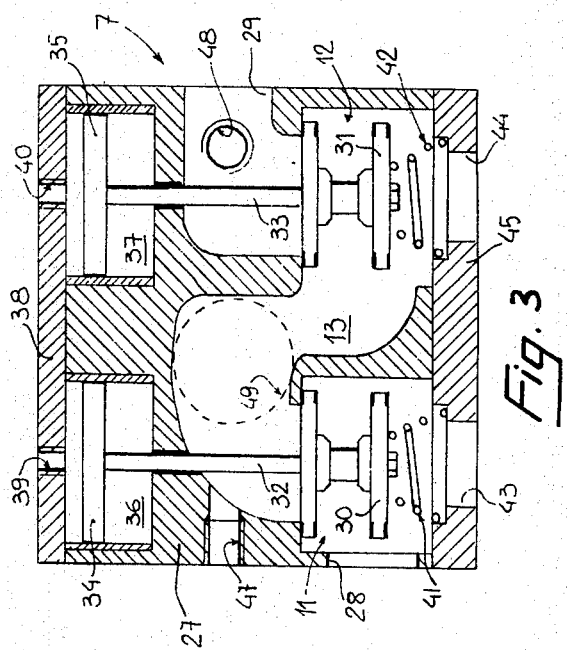
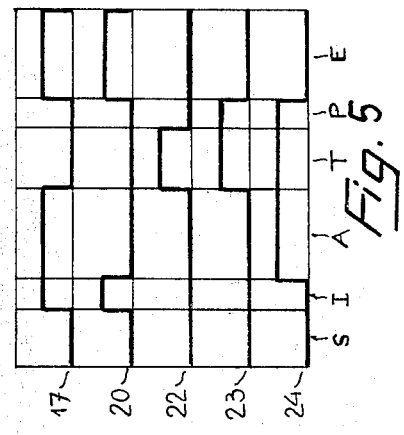
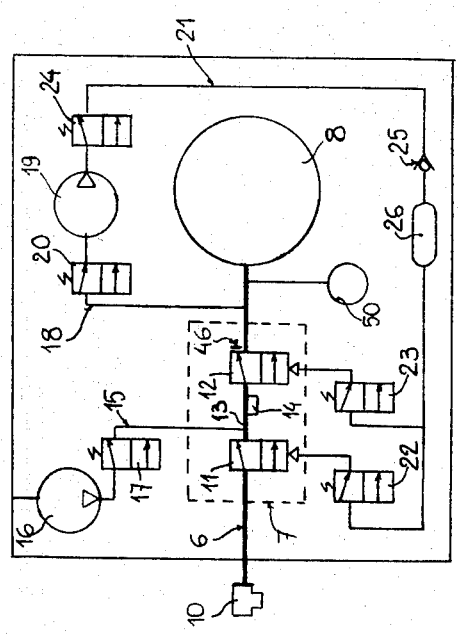
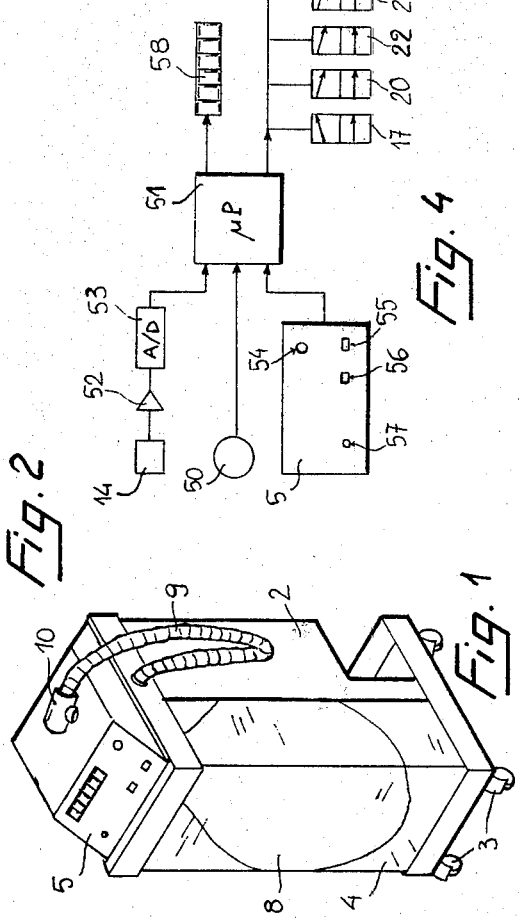

APPARATUS FOR MEASURING OXYGEN CONSUMPTION AND THE EXCHANGE OF OTHER BREATHING GASES

BACKGROUND OF THE INVENTION

This invention relates to an apparatus for measuring oxygen consumption and the exchange of other breathing gases.

In the field of medical diagnostics, the importance of oxygen consumption in a human being, as a parameter of both the body energetic requirements and circulatory events, such as heart flow rate, is well known.

The measuring methods currently employed for this purpose are based upon the measurement of the difference between the amount of oxygen acquired through inhalation and the amount of oxygen exhaled. Therefore, such methods involve a measurement of the volume of gas inhaled in the unit time and the analysis of the oxygen concentration in the inhaled gas, usually envinronmental air, and exhaled gas by the patient. For taking these two different measurements, various instruments are known, which are not devoid of shortcomings, such as lack of accuracy, a very delicate maintenance procedure, and high cost. Also disadvantageous is the complex procedure involved in taking such measurements and the need of carrying out successive calculations, so that those measurements have been limited heretofore to experimental purposes.

SUMMARY OF THE INVENTION

The task of this invention is to provide an apparatus which is capable of taking, in a fully automated manner, measurements of the consumption of oxygen and other breathing gases, both on spontaneously breathing patients and assisted breathing patients, and capable to ensure a high degree of accuracy.

Within said task, it is an object of the invention to provide an apparatus as indicated, which affords the possibility of taking repeated measurements at sufficiently short time intervals.

Another object of this invention is to provide an apparatus as indicated, which is of simple design, compact, easy to service, of convenient use on the patient, and of comparatively low cost.

The aforesaid task and objects are achieved, according to the invention, by an apparatus for measuring oxygen consumption and the exchange of other breathing gases, characterized in that it comprises a variable volume vessel for collecting the gas exhaled by a patient therein, a main pneumatic circuit for connecting said patient to said vessel, an auxiliary circuit for the passage of a reference gas therethrough, said reference gas being the same gas being inhaled by said patient, means for analyzing the percentage of the gas being measured in said exhaled gas and said reference gas, means for emptying said vessel, and means for counting the filling and emptying times of said vessel.

BRIEF DESCRIPTION OF THE DRAWINGS

The features of this invention will be more clearly understood from the following detailed description of a preferred embodiment of this apparatus for measuring oxygen consumption, with reference to the accompanying drawing, where:

FIG. 1 is a general perspective view of this apparatus;

FIG. 2 illustrates a pneumatic diagram of the apparatus;

FIG. 3 is a sectional view of a valving unit in the main pneumatic circuit;

FIG. 4 is a functional block diagram illustrating the connection of electronic control means to this apparatus; and FIG. 5 is a diagram of the operative steps of this apparatus pneumatic members.

DESCRIPTION OF THE PREFERRED EMBODIMENTS

With reference to the drawing figure, there is indicated generally at 1 the apparatus for measuring the consumption of oxygen, according to this invention, which apparatus comprises a housing or frame 2 mounted on caster wheels 3, and having of preference a transparent front wall 4. At the top of the frame 2, a panel 5 is provided which accommodates the apparatus controls, as will be explained hereinafter. Inside the frame 2, the apparatus members are contained which comprise a mechanical-pneumatic section and an electronic control and processing section.

The mechanical-pneumatic section comprises, essentially, gas picking up and analyzing circuits, the operative arrangement whereof is shown in FIG. 2. That section includes a main pneumatic circuit comprising a line or conduit 6 which directly communicates with a flexible bag 8 of great capacity through a valving unit indicated in dotted lines at 7 in FIG. 2. The bag 8, which is preferably made of a material known in the trade as neoprene, serves the function of collecting the exhaled gas from a patient and is visible through the transparent or clear wall 4 of the frame. To enable the collection of exhaled gas, the line 6 is connected, outside of the housing or frame 2, to a hose pipe 9 which carries at its free end a respiratory three-way valve 10, of a type commonly employed for pneumological measurements. The patient will be connected to the respiratory valve 10 through a mouth-piece or respirator, such as to inhale environmental air or another breathing gas from the outside, and to exhale to the apparatus, into the bag 8. The valving unit 7 essentially includes, in a single body, two pneumatically operated valves 11,12 of the three-way type, which valves are arranged serially and adapted for separating along said main circuit a compartment or channel 13 which is equipped with an analyzer 14 of the percentage of the gas being considered. In the specific instance of oxygen consumption measurement, that analyzer will comprise, of preference, an electro-chemical sensor known in the trade as fuel-cell. To the channel 13 there further opens an auxiliary pneumatic circuit which comprises a conduit or line 15 whereon a force compressor 16 is mounted, adavantageously of the diaphragm type, for the circulation of a reference gas therethrough (either environmental air or another mix), which gas is the same gas inhaled by the patient during the test. The conduit 15 is throttled, downstream of the compressor 16, by a three-way solenoid valve 17.

From the main pneumatic circuit, there further branches an emptying conduit 8 connected to the valving unit 7 downstream of the valve 12, on said conduit 8 a second compressor 19 being mounted of the diaphragm suction type, with the interposition of a three-way solenoid valve 20. On the delivery side, the compressor 19 is adapted for applying a pressure to the pneumatic valves 11,12 through a delivery line 21 and solenoid valves 22,23. On the line 21, there are provided a discharge solenoid valve 24, a check valve 25, and a compensation tank 26, in this order.

The valving unit 7 comprises a body 27, preferably of cast metal, wherein there is formed said channel 13 connected to the main line 6 for the exhaled gas, to which line 6 it is connected by means of fittings 28,29, respectively on the patient side and bag side.

The channel 13 is shaped to a double loop or bight, such as to define parallel movement seats for shutters 30,31 of said valves 11,12 actuated, through stems 32,33, by small pistons or plungers 34,35 which are slidable in sealed relationship inside cylindrical chambers 36,37. The chambers 36, 37 are closed by a cover 38 of the body 27, wherethrough there are formed threaded holes 39,40 for transmitting the valve actuating pressure from the conduit or line 21. The shutters 30,31, in the inoperative or rest position thereof, as determined by the bias applied thereto by coil springs 41,42, put said main pneumatic circuit in communication with discharge or exhaust holes 43,44 formed in a base 45 of said body 27. The discharge hole 44 of the valve 12 is normally closed by an automatic valve 46. Lastly, in the body 27, there are formed threaded holes 47 and 48, respectively for connection of the auxiliary conduit 15 and emptying conduit 18. Centrally to the channel 13, there is formed a seat 49 for the fuel-cell sensor 14, which sensor comprises, in a manner known per se, a cylindrical body having on a front face thereof a diaphragm semi-permeable to oxygen, which face must face said channel.

A pressure switch 50 is finally connected to the main pneumatic circuit, in the proximity of the area where the bag 8 is connected to the latter; the pressure switch serves as a monitor device for the emptying of the bag.

The electronic control and processing section, as schematically illustrated in FIG. 4, comprises essentially a microprocessor 51 of the programmable single chip type; in other words, a processor wherein a plurality of electronic circuits are mounted on a single silicon element. The microprocessor is intended for receiving data in the binary form, storing them in a storage memory of its own for subsequent processing, for carrying out aritmetical and logical operations thereon in accordance with programmed instructions, and for supplying the results on an output device.

To the input of the microprocessor 51 are supplied: the electric signal from the sensor 14, as amplified by an amplifier 52 and converted into binary digits by an analog-digital converter 53; the signal from the pressure switch 50; the control pulses introduced by the operator through the pushbuttons of the panel 5, which are a selector 54 of the test duration, a selector 55 of the type of test, whether a single or multiple one, a pushbutton 56 for controlling the start of the test, and a reset pushbutton 57. The microprocessor 51 supplies at the output thereof the control of the operative steps of the valves 17,20,22,23,24, as shown in FIG. 5, and supplies the results of the measurements in digital form on luminous displays 58.

The apparatus just described operates as follows. As the apparatus is turned on, the compressors 16,19 are energized and a voltage is applied to the electronic section, making it ready for the programmed operation. The solenoid valves are switched from the "off" condition S to the "start" condition I, i.e. the valves 17 and 20 are energized; the reference gas flows through the auxiliary circuit 15 to the valving unit 7 and discharges through the automatic valve 46; the fuel cell measures the oxygen concentration in said gas. Simultaneously therewith, the compressor 19 evacuates the bag 8 of any gas contained therein: as the pressure switch 50 signals the emptying of the bag, the valve 20 is again switched and the valve 24 energized thereby the compressor 19 puts the conduit 21 under pressure. The apparatus is held in this situation of standby A until the pushbutton 56 controlling the start of the test is depressed; prior to this, of course, the duration and type of the test should be selected through the selector switches 54,55. At the start of the "test" step T, the valve 17 is switched to deflect the flow of reference gas outwards, and the valves 22,23 are opened which control or drive the pneumatic valves 11,12. The displacement of the shutters 32,33, effective to shut the discharge holes 43,44, allows the gas exhaled by the patient to collect into the bag 8 through the channel 13. At the end of the selected test duration time, the valve 22 only is closed to deflect the gas exhaled by the patient to the discharge hole 43, the channel 13 remaining in communication with the bag 8. During that "break" or rest step P, of fixed duration, the collected gas reaches, by internal diffusion, a homogeneous condition, thereby at the end of that step the fuel cell 14 will read the average value of the oxygen concentration in the gas. That value is then subtracted from that of the oxygen concentration in the reference gas, as stored in the microprocessor 51 a short time before the start of the test phase T.

During the following "processing" step E, the solenoid valves are brought back to their condition at the onset of the start phase I: the reference gas flows through the channel 13, thus scavenging it and, at the same time, the compressor 19 empties the bag 8 at a strictly constant rate. The emptying time, accordingly, is directly proportional to the volume of the collected gas and is counted in the microprocessor 51. The product of that volume by the measured oxygen concentration difference will give the value of the oxygen consumption, which value is displayed, together with the volume value, on luminous displays 58 which are both referred to unit time. At this stage, in the case of a single test, the apparatus returns to its standby condition A, whereas in the case of a multiple test, it initiates automatically successive test steps T, and so forth until the reset pushbutton 57 is depressed.

Obviously, the apparatus described hereinabove may be operated, in accordance with the same principles and with the same cycle, with a sensor other than the fuel cell indicated, to measure both the same oxygen consumption and of the exchange of another breathing gas, in particular carbon dioxide. Advantageously, an apparatus equipped with two different sensors may be provided, for concurrently measuring the oxygen consumption and exchange of carbon dioxide.

I claim:

1. An apparatus for measuring the consumption or exchange of a gas component in breathing gases inhaled or exhaled by a subject over a predetermined period of time, including means sensing the amount of said gas component in the inhaled and exhaled gases and determining the volume of the exhaled gas during said time period, said means providing electrical signals proportionate to said amounts and volume, which are supplied to a data processing unit computing the consumption value, said apparatus comprising:

a variable volume vessel for collecting the exhaled gas, a main pneumatic circuit connecting said subject to said vessel, a pair of valve means arranged along said circuit and defining a compartment in which said sensing means is arranged, a first exhaust opening arranged in said compartment and connecting the latter with the ambient, a second exhaust opening arranged along said circuit between said subject and said compartment and connecting said subject to the ambient, said pair of valve means being movable between a first position in which they close said compartment and a second position in which they close said exhaust openings, an auxiliary circuit for supplying into said compartment the same gas inhaled by the subject, means for controlling said pair of valve means and said auxiliary circuit so that, in said first position, the supplied gas enters said compartment and flows out through said first opening, while the gas exhaled by the subject is deflected into the ambient through said second exhaust opening, whereas, in said second position the supplying of gas into said compartment is interrupted and the exhaled gas flows through said compartment into said vessel, means being further provided for emptying said vessel when the valve means are in said first position.

2. An apparatus as claimed in claim 1, comprising a body in which a channel is formed defining said compartment, said channel being shaped as a double bight to define a pair of parallel movement seats for respective shutters defining said pair of valve means.

3. An apparatus as claimed in claim 2, wherein said shutters are connected through stems with respective pistons slidably arranged in chambers formed in said body and connectable by means of electrically operated valves with a pressure delivery line.

4. An apparatus as claimed in claim 3, wherein said means for emptying said vessel comprise a compressor having its delivery side connected with said pressure delivery line and its suction said connected with said vessel, electrically operated valves being arranged at the delivery and suction side of said compressor and a switch being further provided responsive to the pressure in said vessel and controlling said compressor.

* * * * *